(12) United States Patent
Hoarau

(10) Patent No.: US 7,890,153 B2
(45) Date of Patent: Feb. 15, 2011

(54) SYSTEM AND METHOD FOR MITIGATING INTERFERENCE IN PULSE OXIMETRY

(75) Inventor: Carine Hoarau, Lafayette, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 588 days.

(21) Appl. No.: 11/529,081

(22) Filed: Sep. 28, 2006

(65) Prior Publication Data
US 2008/0081973 A1    Apr. 3, 2008

(51) Int. Cl.
  *A61B 5/1455*  (2006.01)
(52) U.S. Cl. ...................................................... 600/323
(58) Field of Classification Search .................. 600/323, 600/331, 336, 344
See application file for complete search history.

(56) References Cited

U.S. PATENT DOCUMENTS

| | | | |
|---|---|---|---|
| 3,721,813 A | 3/1973 | Condon et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,685,464 A * | 8/1987 | Goldberger et al. | 600/344 |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |

(Continued)

FOREIGN PATENT DOCUMENTS

DE    19632361    2/1997

(Continued)

OTHER PUBLICATIONS

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1919.

(Continued)

*Primary Examiner*—Eric F Winakur

(57) ABSTRACT

A pulse oximetry sensor adapted to emit light from an emitter proximate to a patient's tissue and detect a portion of the emitted light on a detector proximate to the tissue. The pulse oximetry system is adapted to acquire position data for the emitter and for the detector with one or more position indicators. The pulse oximetry system is adapted to process the position data to obtain a change in position of the emitter and the detector; and to process pulse oximetry measurements using the change in position to obtain a motion-corrected pulse oximetry data.

18 Claims, 6 Drawing Sheets

U.S. PATENT DOCUMENTS

| | | | |
|---|---|---|---|
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A * | 6/1991 | Niwa .................... 600/483 |
| RE33,643 E | 7/1991 | Isaacson et al. |
| 5,028,787 A | 7/1991 | Rosenthal et al. |
| 5,035,243 A | 7/1991 | Muz |
| 5,040,039 A | 8/1991 | Hattori et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynksi |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,101,825 A * | 4/1992 | Gravenstein et al. ........ 600/326 |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |

| Patent No. | Date | Inventor(s) |
|---|---|---|
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |

| | | | | | | |
|---|---|---|---|---|---|---|
| 5,842,982 | A | 12/1998 | Mannheimer | 6,067,462 | A | 5/2000 | Diab et al. |
| 5,846,190 | A | 12/1998 | Woehrle | 6,073,038 | A | 6/2000 | Wang et al. |
| 5,851,178 | A | 12/1998 | Aronow | 6,078,833 | A | 6/2000 | Hueber |
| 5,851,179 | A | 12/1998 | Ritson et al. | 6,081,735 | A | 6/2000 | Diab et al. |
| 5,853,364 | A | 12/1998 | Baker, Jr. et al. | 6,081,742 | A | 6/2000 | Amano et al. |
| 5,860,919 | A | 1/1999 | Kiani-Azarbayjany et al. | 6,083,157 | A | 7/2000 | Noller |
| 5,865,736 | A | 2/1999 | Baker, Jr. et al. | 6,083,172 | A | 7/2000 | Baker, Jr. et al. |
| 5,871,442 | A | 2/1999 | Madarasz et al. | 6,088,607 | A | 7/2000 | Diab et al. |
| 5,879,294 | A | 3/1999 | Anderson et al. | 6,094,592 | A | 7/2000 | Yorkey et al. |
| 5,885,213 | A | 3/1999 | Richardson et al. | 6,095,974 | A | 8/2000 | Shemwell et al. |
| 5,890,929 | A | 4/1999 | Mills et al. | 6,104,938 | A | 8/2000 | Huiku et al. |
| 5,891,021 | A | 4/1999 | Dillon et al. | 6,112,107 | A | 8/2000 | Hannula |
| 5,891,022 | A | 4/1999 | Pologe | 6,113,541 | A | 9/2000 | Dias et al. |
| 5,891,024 | A | 4/1999 | Jarman et al. | 6,115,621 | A | 9/2000 | Chin |
| 5,891,025 | A | 4/1999 | Buschmann et al. | 6,122,535 | A | 9/2000 | Kaestle et al. |
| 5,891,026 | A | 4/1999 | Wang et al. | 6,133,994 | A | 10/2000 | Mathews et al. |
| 5,902,235 | A | 5/1999 | Lewis et al. | 6,135,952 | A | 10/2000 | Coetzee |
| 5,910,108 | A | 6/1999 | Solenberger | 6,144,444 | A | 11/2000 | Haworth et al. |
| 5,911,690 | A | 6/1999 | Rall | 6,144,867 | A | 11/2000 | Walker et al. |
| 5,912,656 | A | 6/1999 | Tham et al. | 6,144,868 | A | 11/2000 | Parker |
| 5,913,819 | A | 6/1999 | Taylor et al. | 6,149,481 | A | 11/2000 | Wang et al. |
| 5,916,154 | A | 6/1999 | Hobbs et al. | 6,150,951 | A | 11/2000 | Olejniczak |
| 5,916,155 | A | 6/1999 | Levinson et al. | 6,151,107 | A | 11/2000 | Schöllerman et al. |
| 5,919,133 | A | 7/1999 | Taylor et al. | 6,151,518 | A | 11/2000 | Hayashi |
| 5,919,134 | A | 7/1999 | Diab | 6,152,754 | A | 11/2000 | Gerhardt et al. |
| 5,920,263 | A | 7/1999 | Huttenhoff et al. | 6,154,667 | A | 11/2000 | Miura et al. |
| 5,921,921 | A | 7/1999 | Potratz et al. | 6,157,850 | A | 12/2000 | Diab et al. |
| 5,922,607 | A | 7/1999 | Bernreuter | 6,163,715 | A | 12/2000 | Larsen et al. |
| 5,924,979 | A | 7/1999 | Swedlow et al. | 6,165,005 | A | 12/2000 | Mills et al. |
| 5,924,980 | A | 7/1999 | Coetzee | 6,173,196 | B1 | 1/2001 | Delonzor et al. |
| 5,924,982 | A | 7/1999 | Chin | 6,178,343 | B1 | 1/2001 | Bindszus et al. |
| 5,924,985 | A | 7/1999 | Jones | 6,181,958 | B1 | 1/2001 | Steuer et al. |
| 5,934,277 | A | 8/1999 | Mortz | 6,181,959 | B1 | 1/2001 | Schöllerman et al. |
| 5,934,925 | A | 8/1999 | Tobler et al. | 6,184,521 | B1 | 2/2001 | Coffin, IV et al. |
| 5,940,182 | A | 8/1999 | Lepper, Jr. et al. | 6,188,470 | B1 | 2/2001 | Grace |
| 5,954,644 | A | 9/1999 | Dettling et al. | 6,192,260 | B1 | 2/2001 | Chance |
| 5,960,610 | A | 10/1999 | Levinson et al. | 6,195,575 | B1 | 2/2001 | Levinson |
| 5,961,450 | A | 10/1999 | Merchant et al. | 6,198,951 | B1 | 3/2001 | Kosuda et al. |
| 5,961,452 | A | 10/1999 | Chung et al. | 6,206,830 | B1 | 3/2001 | Diab et al. |
| 5,964,701 | A | 10/1999 | Asada et al. | 6,213,952 | B1 | 4/2001 | Finarov et al. |
| 5,971,930 | A | 10/1999 | Elghazzawi | 6,217,523 | B1 | 4/2001 | Amano et al. |
| 5,978,691 | A | 11/1999 | Mills | 6,222,189 | B1 | 4/2001 | Misner et al. |
| 5,978,693 | A | 11/1999 | Hamilton et al. | 6,226,539 | B1 | 5/2001 | Potratz |
| 5,983,122 | A | 11/1999 | Jarman et al. | 6,226,540 | B1 | 5/2001 | Bernreuter et al. |
| 5,987,343 | A | 11/1999 | Kinast | 6,229,856 | B1 | 5/2001 | Diab et al. |
| 5,991,648 | A | 11/1999 | Levin | 6,230,035 | B1 | 5/2001 | Aoyagi et al. |
| 5,995,855 | A | 11/1999 | Kiani et al. | 6,233,470 | B1 | 5/2001 | Tsuchiya |
| 5,995,856 | A | 11/1999 | Mannheimer et al. | 6,236,871 | B1 | 5/2001 | Tsuchiya |
| 5,995,858 | A | 11/1999 | Kinast | 6,236,872 | B1 | 5/2001 | Diab et al. |
| 5,995,859 | A | 11/1999 | Takahashi | 6,240,305 | B1 | 5/2001 | Tsuchiya |
| 5,997,343 | A | 12/1999 | Mills et al. | 6,253,097 | B1 | 6/2001 | Aronow et al. |
| 5,999,834 | A | 12/1999 | Wang et al. | 6,253,098 | B1 | 6/2001 | Walker et al. |
| 6,002,952 | A | 12/1999 | Diab et al. | 6,256,523 | B1 | 7/2001 | Diab et al. |
| 6,005,658 | A | 12/1999 | Kaluza et al. | 6,256,524 | B1 | 7/2001 | Walker et al. |
| 6,006,120 | A | 12/1999 | Levin | 6,261,236 | B1 | 7/2001 | Grimblatov |
| 6,011,985 | A | 1/2000 | Athan et al. | 6,263,221 | B1 | 7/2001 | Chance et al. |
| 6,011,986 | A | 1/2000 | Diab et al. | 6,263,222 | B1 | 7/2001 | Diab et al. |
| 6,014,576 | A | 1/2000 | Raley et al. | 6,263,223 | B1 | 7/2001 | Sheperd et al. |
| 6,018,673 | A | 1/2000 | Chin et al. | 6,266,546 | B1 | 7/2001 | Steuer et al. |
| 6,018,674 | A | 1/2000 | Aronow | 6,266,547 | B1 | 7/2001 | Walker et al. |
| 6,022,321 | A | 2/2000 | Amano et al. | 6,272,363 | B1 | 8/2001 | Casciani et al. |
| 6,023,541 | A | 2/2000 | Merchant et al. | 6,278,522 | B1 | 8/2001 | Lepper, Jr. et al. |
| 6,026,312 | A | 2/2000 | Shemwell et al. | 6,280,213 | B1 | 8/2001 | Tobler et al. |
| 6,026,314 | A | 2/2000 | Amerov et al. | 6,280,381 | B1 | 8/2001 | Malin et al. |
| 6,031,603 | A | 2/2000 | Fine et al. | 6,285,894 | B1 | 9/2001 | Oppelt et al. |
| 6,035,223 | A | 3/2000 | Baker, Jr. | 6,285,895 | B1 | 9/2001 | Ristolainen et al. |
| 6,036,642 | A | 3/2000 | Diab et al. | 6,285,896 | B1 | 9/2001 | Tobler et al. |
| 6,041,247 | A | 3/2000 | Weckstrom et al. | 6,298,252 | B1 | 10/2001 | Kovach et al. |
| 6,044,283 | A | 3/2000 | Fein et al. | 6,308,089 | B1 | 10/2001 | Von der Ruhr et al. |
| 6,047,201 | A | 4/2000 | Jackson, III | 6,321,100 | B1 | 11/2001 | Parker |
| 6,061,584 | A | 5/2000 | Lovejoy et al. | 6,330,468 | B1 | 12/2001 | Scharf |
| 6,064,898 | A | 5/2000 | Aldrich | 6,334,065 | B1 | 12/2001 | Al-Ali et al. |
| 6,064,899 | A | 5/2000 | Fein et al. | 6,339,715 | B1 | 1/2002 | Bahr et al. |

| | | |
|---|---|---|
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 * | 9/2003 | Aldrich ...................... 600/316 |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,690,958 B1 * | 2/2004 | Walker et al. ............... 600/323 |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |

| Patent No. | Date | Inventor(s) |
|---|---|---|
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | Chin et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | DeLonzor et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,984 B1 | 3/2007 | DeLonzor et al. |
| 7,190,987 B2 | 3/2007 | Lindekugel et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,260,425 B2 | 8/2007 | Chin et al. |
| 7,263,395 B2 | 8/2007 | Chan et al. |
| 7,272,426 B2 | 9/2007 | Scmid |
| 7,280,858 B2 | 10/2007 | Al-Ali et al. |
| 7,305,262 B2 | 12/2007 | Brodnick et al. |
| 7,315,753 B2 | 1/2008 | Baker, Jr. et al. |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0103423 A1 | 8/2002 | Chin et al. |
| 2002/0128544 A1 | 9/2002 | Diab et al. |
| 2002/0133067 A1 | 9/2002 | Jackson, III |
| 2002/0137995 A1* | 9/2002 | Heckel ........................ 600/323 |

| | | | | | | |
|---|---|---|---|---|---|---|
| 2002/0151808 A1* | 10/2002 | Schwartzman et al. ...... 600/512 | 2004/0204636 A1 | 10/2004 | Diab et al. |
| 2002/0156354 A1 | 10/2002 | Larson | 2004/0204637 A1 | 10/2004 | Diab et al. |
| 2002/0173706 A1 | 11/2002 | Takatani | 2004/0204638 A1 | 10/2004 | Diab et al. |
| 2002/0173709 A1 | 11/2002 | Fine et al. | 2004/0204639 A1 | 10/2004 | Casciani et al. |
| 2002/0190863 A1 | 12/2002 | Lynn | 2004/0204865 A1 | 10/2004 | Lee et al. |
| 2002/0198442 A1 | 12/2002 | Rantala et al. | 2004/0210146 A1 | 10/2004 | Diab et al. |
| 2003/0018243 A1 | 1/2003 | Gerhardt et al. | 2004/0215069 A1 | 10/2004 | Mannheimer |
| 2003/0036690 A1 | 2/2003 | Geddes et al. | 2004/0230107 A1 | 11/2004 | Asada et al. |
| 2003/0045785 A1 | 3/2003 | Diab et al. | 2004/0230108 A1 | 11/2004 | Melker et al. |
| 2003/0073889 A1 | 4/2003 | Keilbach et al. | 2004/0236196 A1 | 11/2004 | Diab et al. |
| 2003/0073890 A1 | 4/2003 | Hanna | 2004/0242980 A1 | 12/2004 | Kiani et al. |
| 2003/0100840 A1 | 5/2003 | Sugiura et al. | 2004/0249252 A1 | 12/2004 | Fine et al. |
| 2003/0107568 A1* | 6/2003 | Urisaka et al. ............. 345/419 | 2004/0257557 A1 | 12/2004 | Block et al. |
| 2003/0132495 A1 | 7/2003 | Mills et al. | 2004/0260161 A1 | 12/2004 | Melker et al. |
| 2003/0135099 A1 | 7/2003 | Al-Ali | 2004/0267103 A1 | 12/2004 | Li et al. |
| 2003/0159697 A1* | 8/2003 | Wallace ................ 128/204.26 | 2004/0267104 A1 | 12/2004 | Hannula et al. |
| 2003/0162414 A1 | 8/2003 | Schulz et al. | 2004/0267140 A1 | 12/2004 | Ito et al. |
| 2003/0171662 A1 | 9/2003 | O'Connor et al. | 2005/0004479 A1 | 1/2005 | Townsend et al. |
| 2003/0176776 A1 | 9/2003 | Huiku | 2005/0010092 A1 | 1/2005 | Weber et al. |
| 2003/0181799 A1 | 9/2003 | Lindekugel et al. | 2005/0020887 A1 | 1/2005 | Goldberg |
| 2003/0187337 A1 | 10/2003 | Tarassenko et al. | 2005/0020894 A1 | 1/2005 | Norris et al. |
| 2003/0195402 A1 | 10/2003 | Fein et al. | 2005/0033128 A1 | 2/2005 | Ali et al. |
| 2003/0197679 A1 | 10/2003 | Ali et al. | 2005/0033129 A1 | 2/2005 | Edgar, Jr. et al. |
| 2003/0212316 A1 | 11/2003 | Leiden et al. | 2005/0043599 A1 | 2/2005 | O'Mara |
| 2003/0225323 A1 | 12/2003 | Kiani et al. | 2005/0043600 A1 | 2/2005 | Diab et al. |
| 2003/0225337 A1 | 12/2003 | Scharf et al. | 2005/0049470 A1 | 3/2005 | Terry |
| 2003/0236452 A1 | 12/2003 | Melker et al. | 2005/0049471 A1 | 3/2005 | Aceti |
| 2003/0236647 A1 | 12/2003 | Yoon et al. | 2005/0075550 A1 | 4/2005 | Lindekugel |
| 2004/0006261 A1 | 1/2004 | Swedlow et al. | 2005/0113651 A1 | 5/2005 | Wood et al. |
| 2004/0010188 A1 | 1/2004 | Wasserman et al. | 2005/0113656 A1 | 5/2005 | Chance |
| 2004/0015077 A1* | 1/2004 | Sati et al. ..................... 600/427 | 2005/0177034 A1 | 8/2005 | Beaumont |
| 2004/0024297 A1 | 2/2004 | Chen et al. | 2005/0197548 A1 | 9/2005 | Dietiker |
| 2004/0024326 A1 | 2/2004 | Yeo et al. | 2005/0228248 A1 | 10/2005 | Dietiker |
| 2004/0034293 A1 | 2/2004 | Kimball | 2005/0277819 A1 | 12/2005 | Kiani et al. |
| 2004/0039272 A1 | 2/2004 | Abdul-Hafiz et al. | 2005/0283059 A1 | 12/2005 | Iyer et al. |
| 2004/0039273 A1 | 2/2004 | Terry | 2006/0058594 A1 | 3/2006 | Ishizuka et al. |
| 2004/0054269 A1 | 3/2004 | Rantala et al. | 2006/0084852 A1 | 4/2006 | Mason et al. |
| 2004/0054291 A1 | 3/2004 | Schulz et al. | 2006/0089547 A1 | 4/2006 | Sarussi |
| 2004/0059209 A1 | 3/2004 | Al-Ali et al. | 2006/0106294 A1 | 5/2006 | Maser et al. |
| 2004/0059210 A1 | 3/2004 | Stetson | 2006/0195028 A1 | 8/2006 | Hannula et al. |
| 2004/0064020 A1 | 4/2004 | Diab et al. | 2006/0224058 A1 | 10/2006 | Mannheimer |
| 2004/0068164 A1 | 4/2004 | Diab et al. | 2006/0247501 A1 | 11/2006 | Ali |
| 2004/0087846 A1 | 5/2004 | Wasserman | 2006/0258921 A1 | 11/2006 | Addison et al. |
| 2004/0087852 A1* | 5/2004 | Chen et al. .................. 600/407 | 2006/0276700 A1 | 12/2006 | O'Neil |
| 2004/0092805 A1 | 5/2004 | Yarita | 2007/0032710 A1 | 2/2007 | Raridan et al. |
| 2004/0097797 A1 | 5/2004 | Porges et al. | 2007/0032712 A1 | 2/2007 | Raridan et al. |
| 2004/0098009 A1 | 5/2004 | Boecker et al. | 2007/0032715 A1 | 2/2007 | Eghbal et al. |
| 2004/0107065 A1 | 6/2004 | Al-Ali et al. | 2007/0073121 A1 | 3/2007 | Hoarau et al. |
| 2004/0116788 A1 | 6/2004 | Chernoguz et al. | 2007/0073125 A1 | 3/2007 | Hoarau et al. |
| 2004/0116789 A1 | 6/2004 | Boaz et al. | 2007/0073126 A1 | 3/2007 | Raridan, Jr. |
| 2004/0117891 A1 | 6/2004 | Hannula et al. | 2007/0073128 A1 | 3/2007 | Hoarau et al. |
| 2004/0122300 A1 | 6/2004 | Boas et al. | 2007/0299328 A1 | 12/2007 | Chin et al. |
| 2004/0122302 A1 | 6/2004 | Mason et al. | | | |
| 2004/0133087 A1 | 7/2004 | Ali et al. | FOREIGN PATENT DOCUMENTS | | |
| 2004/0133088 A1 | 7/2004 | Al-Ali et al. | DE | 19640807 | 9/1997 |
| 2004/0138538 A1 | 7/2004 | Stetson | EP | 0127947 | 12/1984 |
| 2004/0138540 A1 | 7/2004 | Baker, Jr. et al. | EP | 0630203 | 12/1994 |
| 2004/0143172 A1 | 7/2004 | Fudge et al. | FR | 2685865 | 7/1993 |
| 2004/0147821 A1 | 7/2004 | Al-Ali et al. | JP | 3245042 | 10/1991 |
| 2004/0147822 A1 | 7/2004 | Al-Ali et al. | JP | 4191642 | 7/1992 |
| 2004/0147823 A1 | 7/2004 | Kiani et al. | JP | 5049625 | 3/1993 |
| 2004/0147824 A1 | 7/2004 | Diab et al. | JP | 6014906 | 1/1994 |
| 2004/0152965 A1 | 8/2004 | Diab et al. | JP | 7001273 | 1/1995 |
| 2004/0158134 A1 | 8/2004 | Diab et al. | JP | 10216115 | 8/1998 |
| 2004/0158135 A1 | 8/2004 | Baker, Jr. et al. | JP | 10337282 | 12/1998 |
| 2004/0162472 A1 | 8/2004 | Berson et al. | JP | 2002224088 | 8/2002 |
| 2004/0171920 A1 | 9/2004 | Mannheimer et al. | JP | 2003210438 | 7/2003 |
| 2004/0171948 A1 | 9/2004 | Terry | JP | 2003275192 | 9/2003 |
| 2004/0176671 A1 | 9/2004 | Fine et al. | JP | 2004089546 | 3/2004 |
| 2004/0181133 A1 | 9/2004 | Al-Ali et al. | JP | 2004248820 | 9/2004 |
| 2004/0181134 A1 | 9/2004 | Baker, Jr. et al. | JP | 2004329607 | 11/2004 |
| 2004/0186358 A1 | 9/2004 | Chernow et al. | JP | 2004351107 | 12/2004 |
| 2004/0199063 A1 | 10/2004 | O'Neil et al. | | | |

| | | |
|---|---|---|
| WO | WO9221281 | 12/1992 |
| WO | WO9403102 | 2/1994 |
| WO | WO9502358 | 1/1995 |
| WO | WO9512349 | 5/1995 |
| WO | WO9749330 | 12/1997 |
| WO | WO9857577 | 12/1998 |
| WO | WO9932030 | 7/1999 |
| WO | WO9947039 | 9/1999 |
| WO | WO02062213 | 8/2002 |
| WO | WO03039326 | 5/2003 |
| WO | WO2005009221 | 2/2005 |
| WO | WO2005010567 | 2/2005 |

OTHER PUBLICATIONS

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Such, Hans Olaf; "Optoelectronic Non-invasive Vascular Diagnostics Using multiple Wavelength and Imaging Approach," *Dissertation*, (1998).

Ferrell, T.L., et al.; "Medical Telesensors," *SPIE*, vol. 3253, pp. 193-198 (1998).

Ikeda, Kenji, et al.; "Improvement of Photo-Electric Plethysmograph Applying Newly Developed Opto-Electronic Devices," *IEEE Tencon*, pp. 1109-1112 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22$^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22$^{nd}$ Annual EMBS International Conference*, Chicago, Illinois; Jul. 23-28, 2000; pp. 2796.

Aoyagi, T., et al.; "Pulse Oximeters: background, present and future," *Neonatal Care*, vol. 13, No. 7, pp. 21-27 (2000) (Article in Japanese—contains English summary of article).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Lopez-Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Cyrill, D., et al.; "Adaptive Comb Filter for Quasi-Periodic Physiologic Signals," *Proceedings of the 25$^{th}$ Annual International Conference of the IEEE EMBS*, Cancun, Mexico, Sep. 17-21, 2003; pp. 2439-2442.

Aoyagi, Takuo; "Pulse oximetry: its invention, theory, and future," *Journal of Anesthesia*, vol. 17, pp. 259-266 (2003).

Itoh, K., et al.; "Pulse Oximeter," *Toyaku Zasshi* (Toyaku Journal), vol. 25, No. 8, pp. 50-54 (2003) (Article in Japanese—contains English summary of article).

Johnston, William S., et al.; "Effects of Motion Artifacts on helmet-Mounted Pulse Oximeter Sensors," 2 pgs. (2004).

Matsuzawa, Y., et al.; "Pulse Oximeter," *Home Care Medicine*, pp. 42-45 (Jul. 2004); (Article in Japanese—contains English summary of article).

Odagiri, Y.; "Pulse Wave Measuring Device," *Micromechatronics*, vol. 42, No. 3, pp. 6-11 (undated) (Article in Japanese—contains English summary of article).

\* cited by examiner

SYSTEM AND METHOD FOR MITIGATING INTERFERENCE IN PULSE OXIMETRY

BACKGROUND OF THE INVENTION

1. Field of the Invention

The present invention relates generally to pulse oximetry and, more particularly, to mitigation of interference in pulse oximetry.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically senses the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms. Changes in the amount of arterial blood in the tissue during a blood pressure pulse may change the amount and character of the light detected by the sensor's photodetector.

Normally, obtaining pulse oximetry measurements involves physically attaching a sensor to an anatomical part, whereby the attachment can be accomplished in various ways, depending on the type of sensor and the anatomical part in question. Accordingly, this attachment can substantially influence the quality of the pulse oximetry measurement, which depends on the sensor's ability to detect changes in the concentration of arterial blood relative to other tissue structures in the portion of the tissue illuminated by the sensor. Therefore, motion of the sensor relative to the tissue or changes in tissue during a pulse oximetry measurement, such as voluntary or involuntary movements can lead to changes in the spatial relationship between the sensor and the tissue. Consequently, the light's optical path can change, which may cause the light emitted by the sensor to interact with different tissue structures and tissue surfaces having different levels of blood perfusion and/or different absorption scattering characteristics. Thus, the motion of the sensor relative to the tissue can result in variations of light intensities detected by the sensor during the measurement process, adversely affecting the values of physiological parameters derived from a pulse oximetry measurement. Such related-variations and aberrations within the derived data are typically referred to as interference. Unfortunately, such interference may give a false indication on the state of the physiological parameter being measured, and thus, degrade the accuracy and reliability of the physiological parameter obtained.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Accordingly, the following technique describes a system and method for mitigating interference in pulse oximetry and to thereby increase the accuracy and reliability of any physiological parameters derived form the pulse oximetry measurement thereof. Specifically, it is desirable to have at least one position indicator that can measure the positions of one or more reference points in space and time, such as for example, the orientation of the emitter with respect to the detector at any point in time. Moreover, the data acquired by the position indicator should be processed synchronously with the pulse oximetry data to reduce noise in the pulse oximetry data or other physiological parameters.

Figure 1:
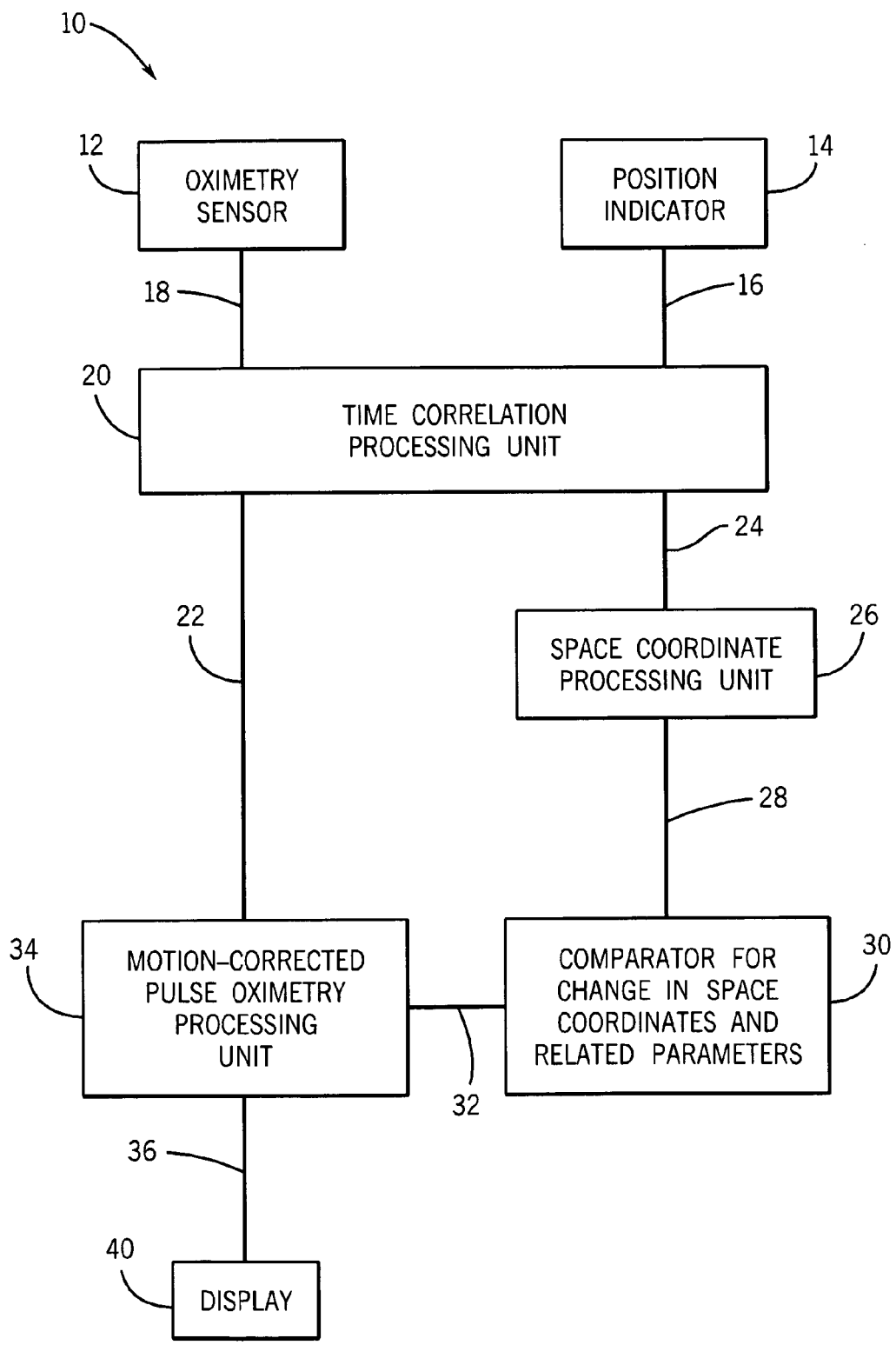
FIG. 1 illustrates a block diagram of a system configured to generate motion-corrected pulse oximetry parameters in accordance with one aspect of the present technique.

Referring to FIG. 1, a technique is depicted for acquiring and using positional and pulse oximetry data to mitigate interference. In particular, block diagram 10 illustrates an embodiment of the present technique utilizing time correlated acquisition and processing of pulse oximetry and position data. As such, embodiment 10 depicts the manner in which initial uncorrected pulse oximetry data is corrected to yield pulse oximetry physiological parameters having less noise and interference.

System 10 comprises a sensor 12 that acquires pulse oximetry data 18. A position indicator 14 acquires position data 16 of the emitter and the detector of the pulse oximetry sensor 12. A processing unit 20, such as a CPU or microprocessor typically found on a general or special purpose computer or patient monitor, acquires and correlates the pulse oximetry data 18 and the position data 16 for further processing.

The time correlated position data 24 is processed, such as by a processing unit 26, to generate coordinate data 28 which describes the position of the emitter and detector in space and time. Coordinate data 28 is analyzed and compared over time, such as by processing unit 30, to determine changes in the position of the emitter and/or detector over a certain interval of time. As will be appreciated by those of ordinary skill in the art, the various processing units and comparators 20, 26, 30 and 34 discussed herein may in practice be one or more CPU's, microprocessors or dedicated processing circuits located on a general or special purpose computer or patient monitor.

The changes in the position of the emitter and the detector when identified may be used to calculate correction factors/parameters 32, such as, the optical path length between the emitter and the detector of the sensor 12. Correspondingly, processing unit 34 receives corrections factors/parameters 32 from processing unit 30 along with time-correlated pulse oximetry data 22 and calculates corrected pulse oximetry data 36 based on the position of the emitter and detector during acquisition of the respective pulse oximetry data 18. In the process of doing so, processing unit 34 may employ various algorithms and data banks when it corrects the data 22 for interference.

The processing unit 34 may employ a data bank of optical path lengths as a function of light scatter/absorbance probabilities. Thus, for example, patient motion leading to an increase in the optical path length between light emitting and receiving components of the sensor 12 can lead to an increase of light absorption in the tissue. This would be indicated in data 18 as a decrease in the amount of light received by the sensor 12. Accordingly, upon detecting a change in the optical path length, processing unit 34 would correct for the excess absorbance by utilizing absorbance probabilities/optical path length functions. Hence, interference is eliminated by combining time-correlated pulse oximetry data 22 with correction data 32 to yield corrected pulse oximetry data 36. Lastly, the corrected data 36 may be transferred to a display 40 for review by a health care provider.

Figure 2A:
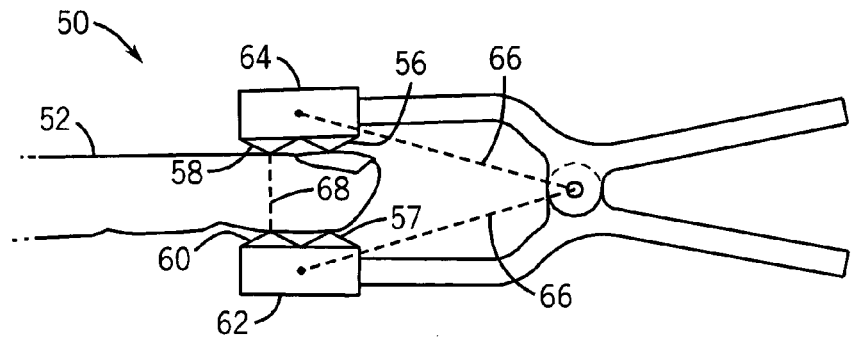
FIGS. 2A, 2B, and 2C, illustrate a cut-away side view of an exemplary clip-style pulse oximetry sensor on a patient's finger in accordance with one aspect of the present technique.
Figure 2B:
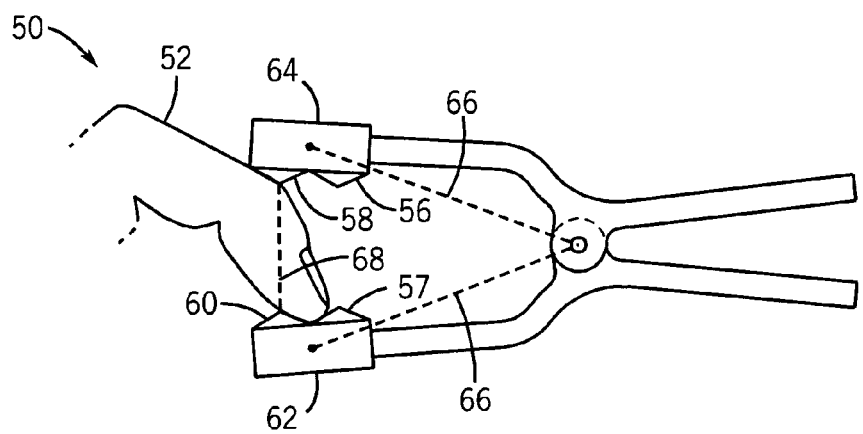
Figure 2C:
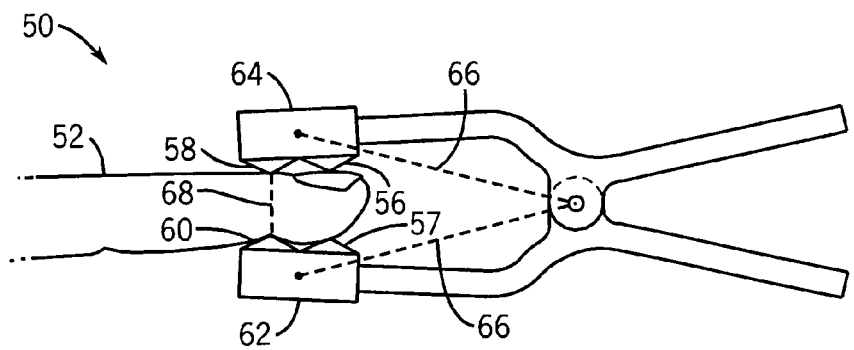

A pulse oximetry sensor which detects motion and generates the pulse oximetry data 18 and the position data 16 for use in system 10 is depicted in FIGS. 2A-2C. Accordingly, these figures illustrate an exemplary clip-style pulse oximetry sensor typically placed on a patient in a location, such as a digit, that is normally perfused with arterial blood to facilitate proper light absorption. However, other common sensor sites include a patient's toes or earlobes. Pulse oximetry sensors used on these sensor sites are typically "transmission type" sensors. Transmission type sensors include an emitter and detector that are typically placed on opposing sides of the sensor site. If the sensor site is a fingertip, for example, the cuff, clip, or bandage associated with the pulse oximetry sensor is positioned over the patient's fingertip such that the emitter and detector lie on either side of the patient's nail bed. In other words, the sensor is positioned so that the emitter is located on the patient's fingernail and the detector is located 180° opposite the emitter on the patient's finger pad. During operation, the emitter shines one or more wavelengths of light through the patient's fingertip, and the light received by the detector is processed to determine various physiological characteristics of the patient. For determining the oxygen saturation of the patient's arterial blood, two or more wavelengths are used, most commonly red and near infrared wavelengths.

Accordingly, FIGS. 2A-2C illustrate a sensor 50 and different postures a digit 52 may attain relative to the sensor 50, as a result of patient motion. As such, variations of the digit's posture may lead to variations in the amount of light scattered or absorbed between emitter and detector of the sensor 50. For example, FIG. 2A illustrates a digit in a neutral posture relative to the sensor 50, such that the clip-portion of the sensor 50 is open in a regular width. However, motion of the digit 52, as illustrated in FIG. 2B, may result in a flexed digit-sensor posture which may lead to a wider opening of the clip. Consequently, this may influence the amount of light that reaches the detector. Similarly, a patient pressing the finger against the clip while the clip is situated on a hard surface, may lead to a narrower opening of the clip, as illustrated in FIG. 2C. This, too, may influence the amount light scattered/absorbed by the tissue.

More specifically, sensor 50 of FIGS. 2A-2C is configured to provide position data 16 (FIG. 1) for the emitter 56 and detector 57, thereby allowing motion correction of pulse oximetry data 18 (FIG. 1) acquired by the sensor 50. Sensor 50 comprises a sensor body that includes the emitter 56, detector 57, and one or more position indicators 58 and 60 proximate to at least one of the emitter 56 and or detector 57. In the configuration shown, the finger clip comprises rigid bottom and top portions 62 and 64 respectively. Accordingly, as the clip opens or closes, the bottom and top portions 62 and 64 are free to move on a vertical plane.

Mounted on structures 62 and 64 are emitter 56 and detector 57 respectively. Similarly, mounted on structures 62 and 64 are position indicators 58 and 60 respectively. The position indicators 58 and 60 are disposed laterally to the emitter 56 and detector 57, respectively, and are separated from them by a known, fixed distance.

The separation distance between the center of each of the portions 62 and 64 and the center of clip is denoted by a line 66. Similarly, the separation distance between position indicators 58 and 60 is denoted by line 68, determined by the opening of the clip. Hence, the space coordinates of the emitter 56 and the detector 57 are obtainable once the separation distances 66 and 68 are known.

Determining the separation distance 64 can be done in various ways. An exemplary method would be to adapt the position indicators 58 and 60 as contact points of a linear resistor embedded in a linear potentiometer device. Accordingly, in a configuration where the digit 52 acts as a variable linear resistor while it is placed between the two indicators 58 and 60, a voltage across the finger can be used to correlate to the distance between the contact points 58 and 60. Hence, the voltage across the digit 52 is directly correlated to the optical path length between the emitter 56 and the detector 57. Thus, motion of the digit 52 relative to the sensor body may cause a change in the position of the digit 52 relative to the emitter 56 and/or the detector 57. Correspondingly, a change in the distance between the contacts 58 and 60 is anticipated as well, as illustrated in FIGS. 2B and 2C. Thus, the displayed configuration establishes correlations between measured potentiometer voltages and digit dislocations. Accordingly, a suitable algorithm can be employed in which changes in measured potentiometer voltages can used to the correct interference in pulse, as discussed with reference to FIG. 1. As will be appreciated by those of ordinary skill in the art, other types of potentiometers may also be similarly employed. For example, potentiometers that measure bending or flex of a substrate by changes in resistance may be employed in place of the linear potentiometer described above to derive the same or analogous spatial data. An example of such a potentiometer is the Bend Sensor® available from Flexpoint®.

Alternatively, employing magnetic field variation sensing using devices, such as Hall Effect Devices, Magneto-Resistive Devices, magnets, and the like are means for providing spatial data for mitigating interference. Applying such means in pulse oximetry may, for example, be useful in determining parameters, such as the optical path length between the emitter and the detector of a pulse oximetry sensor.

Figure 3A:
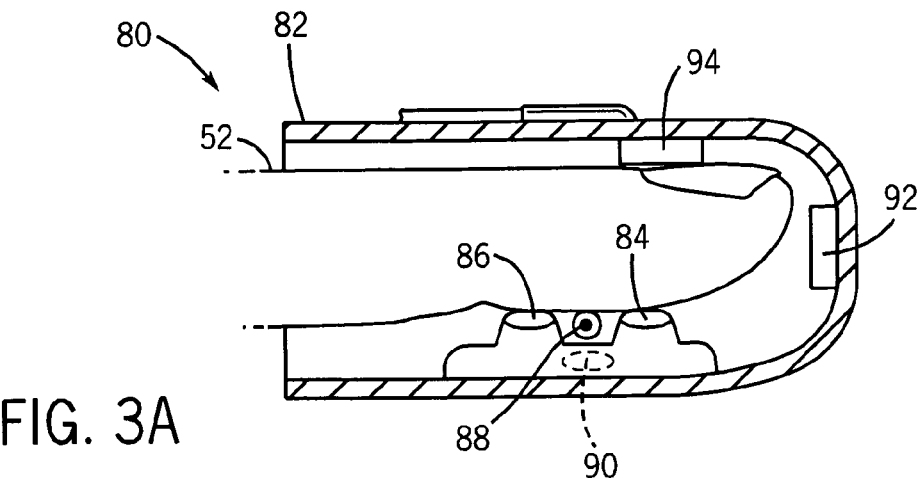
FIGS. 3A, B and C illustrate a cross-sectional view of a pulse oximetry sensor enclosing a patient's digit in accordance with one aspect of the present technique.
Figure 3B:
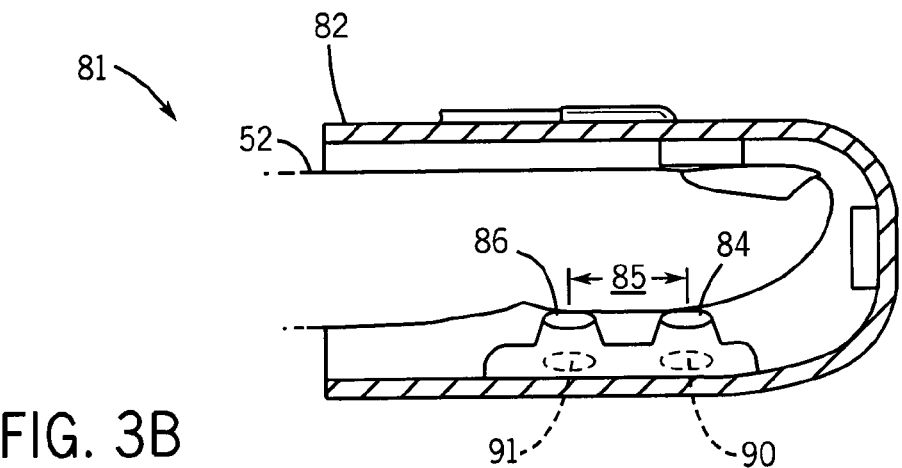
Figure 3C:
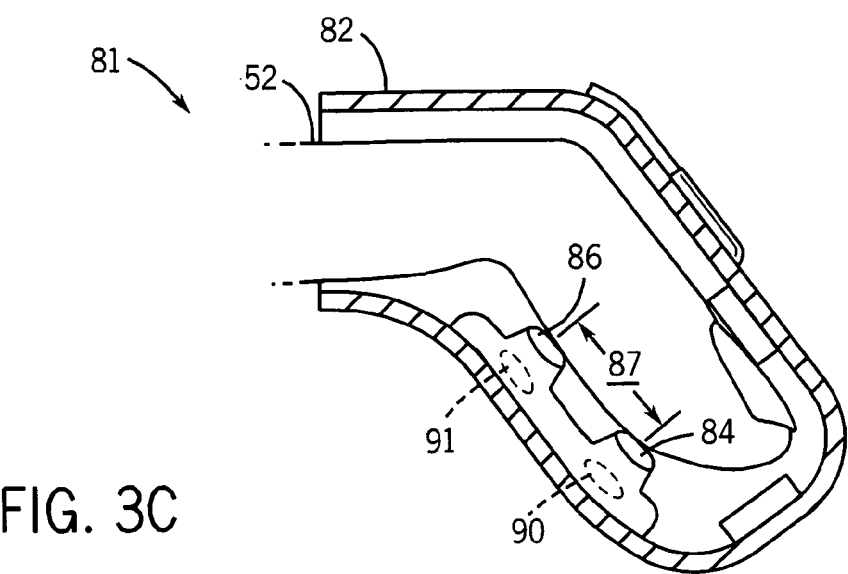

Accordingly, exemplary embodiments of the present technique which utilize magnetic field variation sensing are depicted in FIGS. 3A-3C. An embodiment in accordance with the present technique shown by sensor 80 illustrates a sensor body 82 that completely or partially encloses a patient's digit 52. On the inner surface of the enclosure are an emitter 84 and a detector 86, both pointing upward and toward the digit 60. Accordingly, in this configuration the pulse oximeter sensor 80 is adapted to work in reflectance mode. Reflectance type sensors generally operate under the same general principles as transmittance type sensors. However, reflectance type sensors include an emitter and detector that are typically placed on the same side of the sensor site. For example, sensor 82 depicts an emitter 84 latterly disposed to a detector 86. Photons emitted by the emitter 84 are scattered and reflected off the digit 52 to the detector 86.

Furthermore, embedded inside the enclosure 82 are position sensors 90-94. Hence, the embodiment shown displays a position marker 88, such as a magnet, disposed on the patient's digit 52. Further, the three position sensor 90-94 may be configured as Hall Effect Devices disposed perpendicularly to each other. Furthermore, each position sensor is disposed from the emitter 84 and the detector 86 by a fixed distance. Thus, position marker 88 disposed on the patient's finger may provide a reference point to each of the three position sensors 90-94. Consequently, the three position sensors 90-94 may provide a three dimensional coordinate of the position marker 88 using, for example, a triangulation method.

Accordingly, during pulse oximetry data acquisition, motion of the patient's finger relative to the enclosure 82 brings about a change in position of the position marker 88 with respect to the position sensors 90-94. As such, sensor 80 can acquire data representing the coordinates of the patient's digit 52 relative to the emitter 84 and/or the detector 86.

In a further embodiment shown in FIG. 3B, sensor 80 is configured to determine a separation distance, denoted by reference numeral 85, between the emitter 84 and the detector 86 independent of their separation from the digit 52. Thus, an exemplary configuration may include, position sensor 90 comprising a Hall Effect device, and a position marker 91 comprising a magnet, disposed directly beneath the emitter 84 and the detector 86 respectively. Such a configuration may track the separation between the emitter 84 and the detector 86 as the digit 52 moves.

The foregoing configuration may also be useful in an exemplary embodiment shown in FIG. 3C, where the sensor body 82 of sensor 81 is a flexible enclosure fitted over a patient's flexed finger 52. Accordingly, motion of the digit 52 can cause a deformation of the sensor body, as it stretches and squeezes in various forms. The deformation may bring about a change in the distance between the emitter 84 and the detector 86, as denoted by distance 87. Accordingly, in a flexed posture, distance 87 may be greater or less than distance 85 (FIG. 3B). Hence the difference between the distances 85 and 87 may correspond to a change of the light's optical path as the digit 52 changes its posture. Thus, as the Hall Effect Device disposed in position sensor 90 moves relative to the magnet disposed in position marker 91 during the deformation of the sensor body, a voltage is generated across the Hall Effect device. This can be used to extrapolate the displacement of the emitter 84 relative to the detector 86. Using the position data generated by the relative motion of position sensor 90 and position marker 91, a suitable algorithm may be employed for mitigating pulse oximetry interference, as discussed with reference to FIG. 1.

Figure 4:
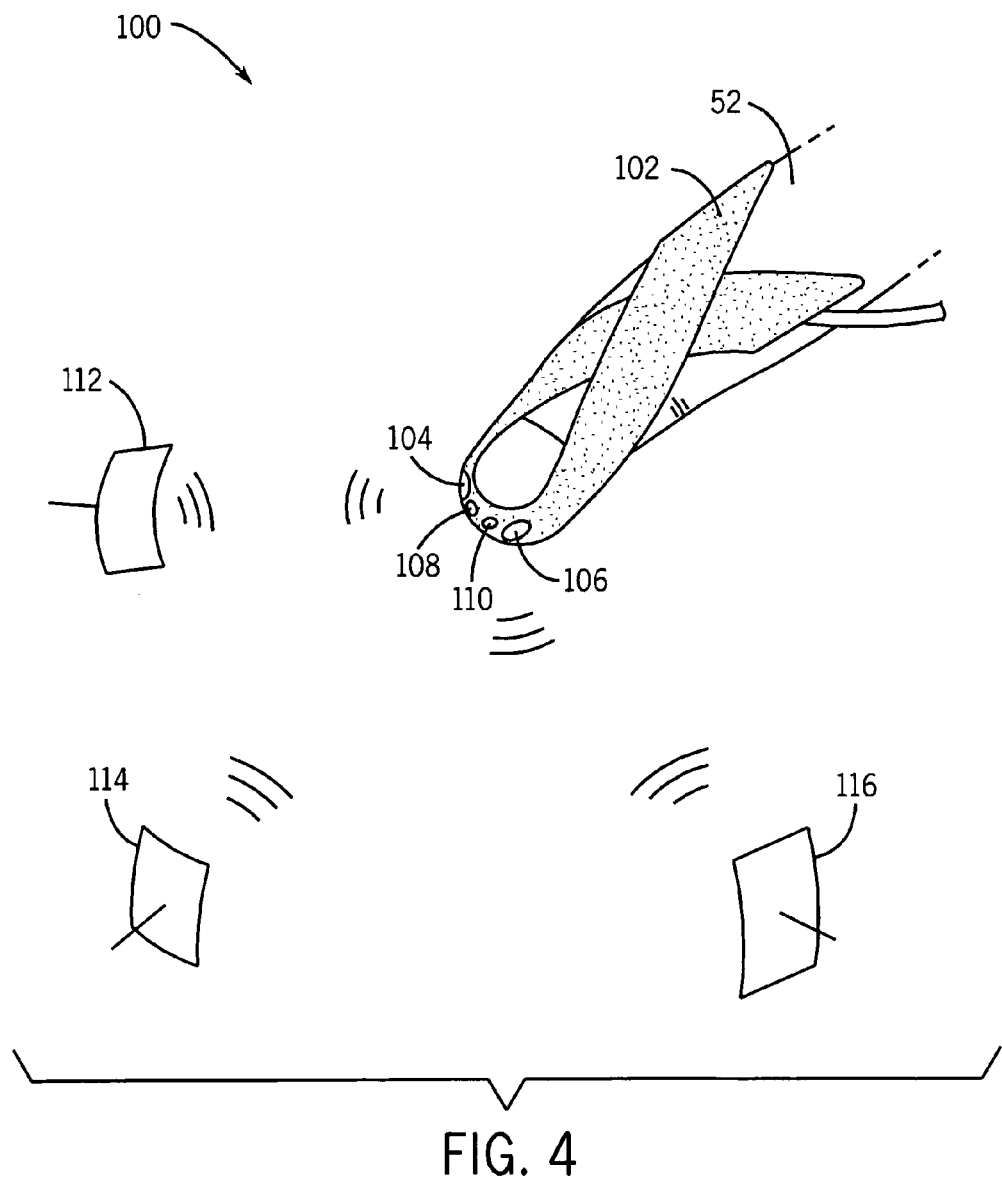
FIGS. 4 and 5 illustrate a top view of a bandage-style pulse oximetry sensor on a patient's finger in accordance with one aspect of the present technique.

Further, an embodiment of a remote positioning system including a pulse oximetry sensor and one or more position sensors is illustrated in FIG. 4. A sensor 100 includes a sensor body 102 in the form of a flexible bandage placed on a patient's digit 52. An emitter 104 and a detector 106 working in transmission mode are disposed on the sensor body 102. Accordingly, finger motion may cause stretching and/or compressing of the bandage-style sensor 102, leading to relative motion between the emitter 104 and the detector 106. Such motion may influence physical measurements on which derived pulse oximetry parameters depend, such as, the optical path length between the emitter 104 and the detector 106. In this embodiment, a combination of local and remote components provides the desired position data. Such components may include active and/or passive devices, markers, and/or media capable of emitting, receiving, reflecting, and/or absorbing electromagnetic radiation.

Thus, in the exemplary embodiment of FIG. 4, tracking the position of the emitter 104 and the detector 106 may be achieved with position sensors 108 and 110 disposed locally and in close proximity to the emitter 104 and the detector 106. For example, the position sensors 108 and 106 may each comprise an RF/IR transmitter configured to transmit a distinct RF/IR frequency. Correspondingly, receivers 112-116 disposed remotely from the sensor body 102 may be configured to receive the distinct RF/IR signals transmitted by the transmitters 108 and 110. Furthermore, the receivers 112-116 may be placed in a manner wherein each of the receivers is disposed perpendicularly to the other two receivers. Signals emitted by the transmitters 108 and 110 can be traced by the receivers 112-116 for triangulating the respective positions of the transmitters 108 and 106.

Figure 5:
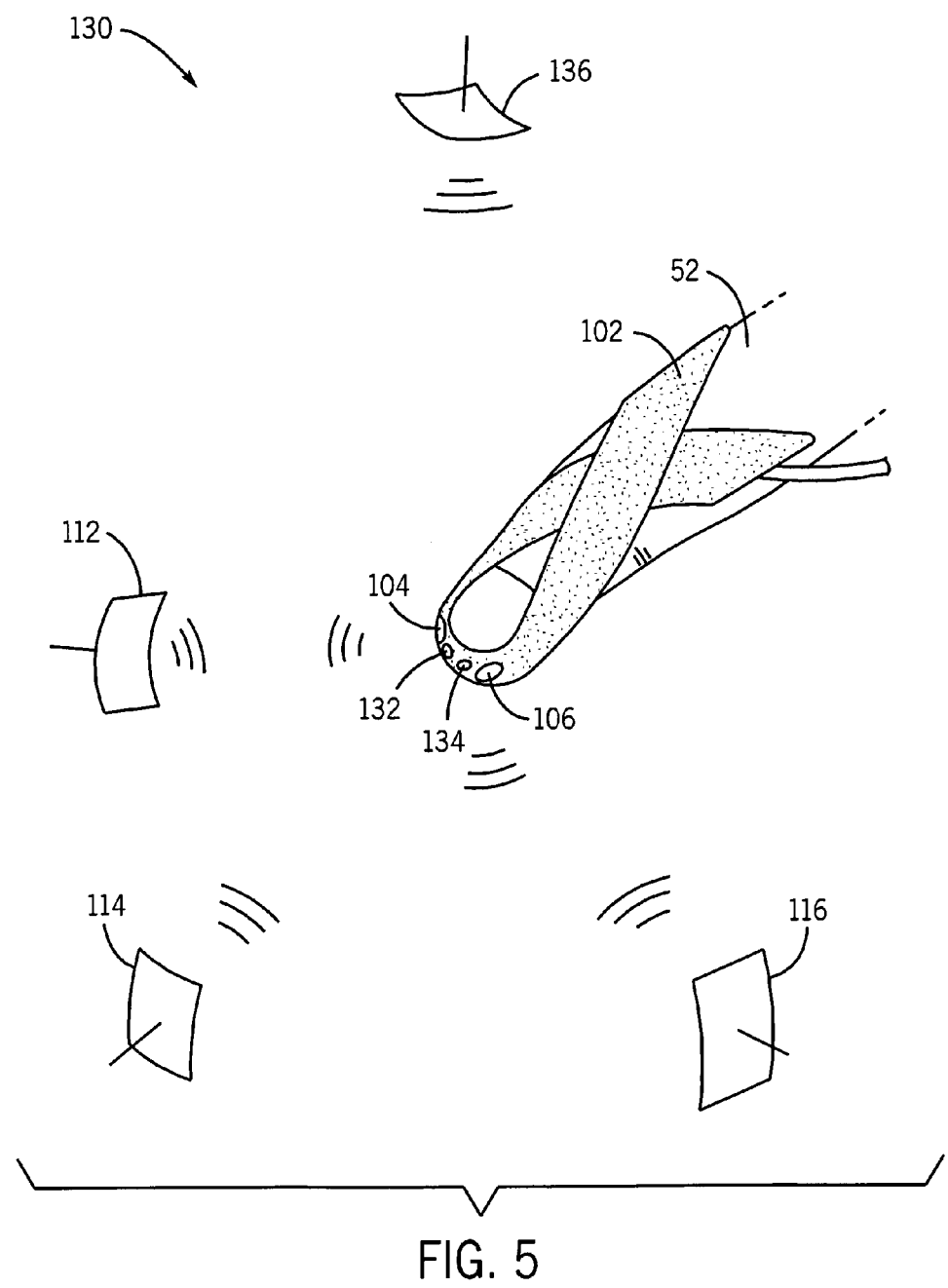

In another exemplary embodiment, as shown by FIG. 5, a sensor 130 with the sensor body 102 includes local position markers 132 and 134 disposed in close proximity to the emitter 104 and the detector 106. Accordingly, the position markers 132 and 134 may be configured as RF/IR reflectors illuminated by transmitter 136. Accordingly, the transmitter 136 may be configured as an RF/IR transmitter capable of transmitting at least two distinct RF/IR frequencies. These frequencies may be received by the receivers 112-116 configured to receive each of the frequencies reflected by position markers 132 and 134. Hence, by triangulation, the configuration above allows to obtain the coordinates of the emitter 104 and the detector 106. Accordingly, this data can be used to correct for interference resulting from unavoidable bandage and/or finger motion as discussed with reference to FIG. 1.

As one skilled in the art would appreciate, position indicator devices for mitigating interference in pulse oximetry are not limited to the ones that have been described thus far. There exist a multitude of other devices that can accomplish the same task such as: accelerometers, fiber optic sensors, interferometers, piezoelectric crystals, pressure gauges, magnetoresistive sensors and more.

Figure 6:
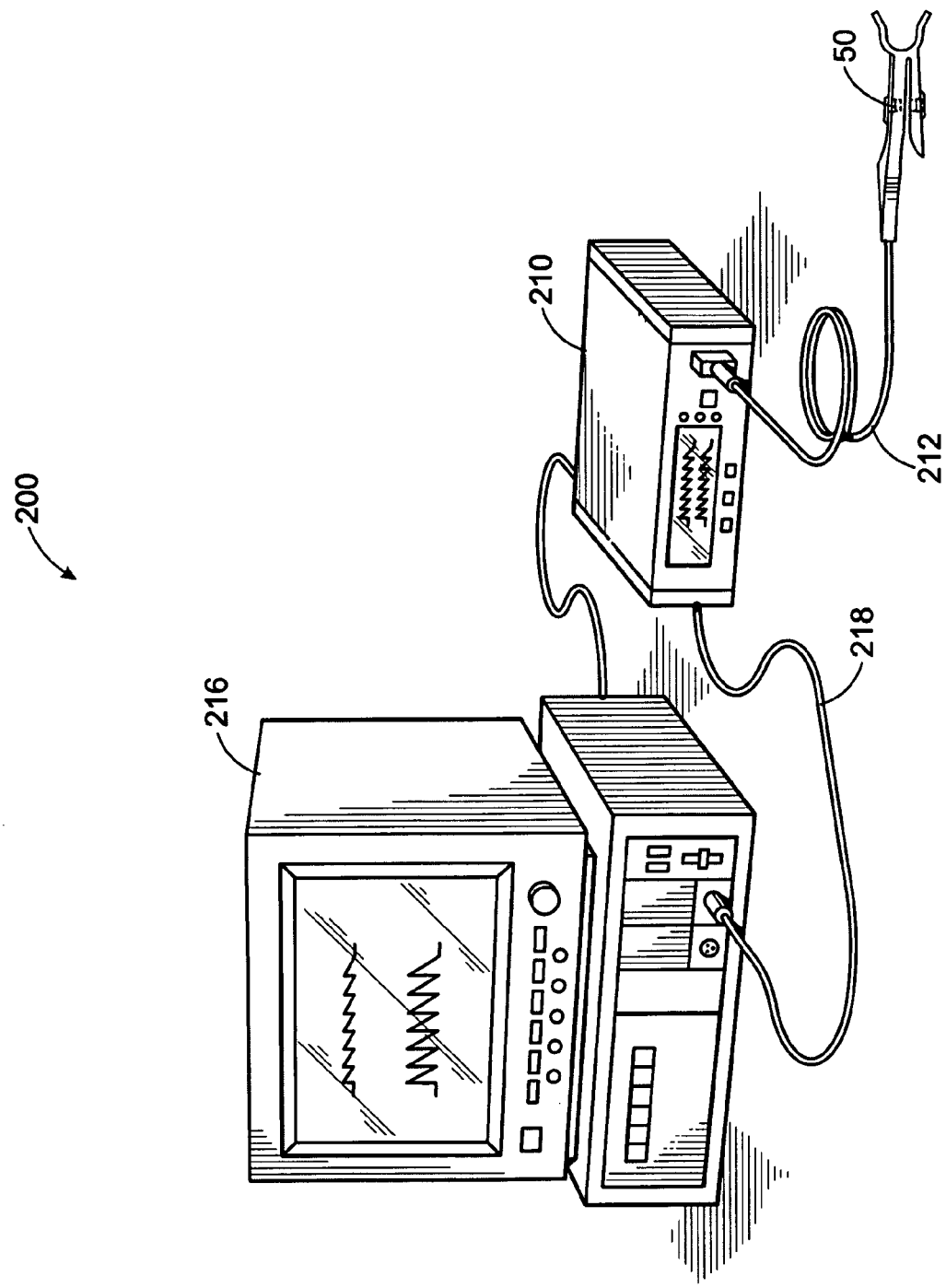
FIG. 6. illustrates a pulse oximetry system coupled to a multi-parameter patient monitor in accordance with one aspect of the present technique.

Regardless of type, the sensors 50, 80, 100, and 130 are typically adapted to be coupled directly to a pulse oximetry system 200 shown in FIG. 6. The system 200 includes a monitor 210, connected to a computer 216 via cable 218. The monitor 210 is also connected to a pulse oximetry sensor 50, 80, 100, 130 via cable 212. However, it should be appreciated that the cable 212 may be coupled to a transmission device (not shown) to facilitate wireless transmission between the sensor 50, 80, 100, 130 the monitor 210. The monitor 210 may be any suitable pulse oximeter, such as those available from Nellcor Puritan Bennett Inc.

What is claimed is:

1. A pulse oximetry system comprising;
   a sensor body having, an emitter, a detector, and one or more position indicators;
   one or more position receivers separate and external from the sensor body and configured to determine the respective positions of the position indicators; and
   a processor-based monitor configured to determine changes in absolute position in space of the sensor body based on the positions determined by the one or more position receivers and to process pulse oximetry measurements from the detector using the changes in absolute position to obtain a motion-corrected pulse oximetry measurement.

2. The pulse oximetry system, as set forth in claim 1, wherein the processor-based monitor utilizes triangulation to determine the change in the absolute position of the sensor body.

3. The pulse oximetry system, as set forth in claim 1, wherein the processor-based pulse oximetry system comprises a display configured to display corrected pulse oximetry data.

4. The pulse oximetry system, as set forth in claim 1, wherein the absolute position comprises coordinates denoting the position in space of the sensor body.

5. A pulse oximetry system comprising;
   a sensor body comprising;
   an emitter;
   a detector;
   one or more position indicators adapted to detect a change in position of at least one of the sensor body, the emitter, or the detector;
   and
   a processor-based monitor configured to process pulse oximetry measurements from the detector using the change in position to obtain a corrected pulse oximetry measurement, wherein the processor-based monitor utilizes a data bank of light scatter/absorbance probability as a function of an optical path length to obtain the corrected pulse oximetry measurement.

6. The pulse oximetry system, as set forth in claim 5, wherein the change in position comprises a change in position of the emitter relative to the detector.

7. The pulse oximetry system, as set forth in claim 5, wherein the change in position comprises an absolute position change of the emitter or the detector.

8. The pulse oximetry system, as set forth in claim 5, wherein absolute position of the emitter or the detector is measured using a Hall effect device.

9. A tangible machine readable medium comprising:
   code for emitting light from an emitter proximate to a patient's tissue;
   code for detecting a portion of the light on a detector proximate to the tissue;
   code for acquiring three-dimensional data for the emitter or for the detector with one or more position indicators;
   code for processing the three-dimensional data to determine if there has been a change in position of the emitter or the detector;
   code for processing pulse oximetry measurements from the detector; and
   code for correcting the pulse oximetry measurements based at least in part on the change in position of the emitter or detector utilizing a data bank of light scatter/absorbance probability as a function of the optical path length.

10. The tangible machine readable medium, as set forth in claim 9, wherein the absolute position data of the emitter or the detector comprises data obtained from a Hall Effect Device.

11. The tangible machine readable medium, as set forth in claim 9, wherein the absolute position data of the emitter or the detector comprises data obtained from a RF/IR remote positioning system.

12. The tangible machine readable medium, as set forth in claim 9, comprising code for determining an optical path length between the emitter and the detector.

13. The tangible machine readable medium, as set forth in claim 9, comprising code for displaying the corrected pulse oximetry measurements.

14. A method for performing pulse oximetry comprising the acts of:
    emitting light from an emitter proximate to a patient's tissue;
    detecting a portion of the emitted light on a detector proximate to the tissue;
    acquiring three-dimensional data for the emitter and for the detector with one or more position indicators;
    processing the three-dimensional data to determine if there has been a change in position of the emitter or the detector;
    processing pulse oximetry measurements from the detector; and
    correcting the pulse oximetry measurements based at least in part on the change in position of the emitter or the detector by utilizing a data bank of light scatter/absorbance probability as a function of an optical path length.

15. The method, as set forth in claim 14, wherein acquiring absolute position data comprises:
    measuring the position of the emitter and the detector by a Hall Effect Device and a magnet.

16. The method, as set forth in claim 14, wherein acquiring absolute position data comprises:
    measuring the position of the emitter and the detector by a remote RF/IR position sensor.

17. The method, as set forth in claim 14, comprising determining an optical path length between the emitter and the detector.

18. The method, as set forth in claim 14, comprising the act of displaying corrected pulse oximetry data.

* * * * *